United States Patent [19]

Onohara et al.

[11] Patent Number: 4,834,721

[45] Date of Patent: May 30, 1989

[54] THERMOPLASTIC RESIN SILICONE COMPOSITE SHAPED ARTICLE

[75] Inventors: Masayuki Onohara, Kanagawa; Kenji Kawai, Yokohama; Masaru Shibata, Kanagawa; Akira Igaras, Yokohama; Nobuhisa Kawaguch, Kamakura, all of Japan

[73] Assignees: Sumitomo Bakelite Company LTD; Fuji Systems Corp., both of Tokyo, Japan

[21] Appl. No.: 151,312

[22] Filed: Feb. 1, 1988

Related U.S. Application Data

[62] Division of Ser. No. 917,194, Oct. 9, 1986, which is a division of Ser. No. 675,997, Nov. 29, 1984, Pat. No. 4,686,124.

[30] Foreign Application Priority Data

| | | |
|---|---|---|
| Dec. 12, 1983 [JP] | Japan | 59-232809 |
| Dec. 26, 1983 [JP] | Japan | 59-244187 |
| Feb. 24, 1984 [JP] | Japan | 58-32607 |
| Feb. 24, 1984 [JP] | Japan | 58-32608 |
| Feb. 24, 1984 [JP] | Japan | 59-32609 |
| Mar. 6, 1984 [JP] | Japan | 59-41457 |
| Mar. 26, 1984 [JP] | Japan | 59-56254 |

[51] Int. Cl.$^4$ ............................................ A61M 25/00
[52] U.S. Cl. ........................................ 604/266; 428/451
[58] Field of Search .......................... 604/265, 408, 266

[56] References Cited

U.S. PATENT DOCUMENTS 4,490,420  12/1984  Yoshida .............................. 428/447
4,582,762   4/1986  Onohara et al. .................... 428/447

*Primary Examiner*—Allan M. Lieberman
*Attorney, Agent, or Firm*—Browdy & Neimark

[57] ABSTRACT

A thermoplastic resin-silicone composite shaped article comprising (a) a shaped article of a thermoplastic resin selected from the group consisting of olefin resins, urethane resins and styrene resins and (b) a cured layer of an additional polymerization type silicone composition adhering to the one or both surfaces of the shaped article of a thermoplastic resin. To the surface of the above shaped article of a thermoplastic resin to which the above cured layer of an additionl polymerization type silicone composition does not adhere, there may adhere another cured layer of the above addition polymerization type silicone composition. To either or both of these cured layers, there may further adhere a layer of the above thermoplastic resin, other thermoplastic resin, a silicone rubber, a silicone resin, glass, ceramics or a metal.

7 Claims, No Drawings

THERMOPLASTIC RESIN SILICONE COMPOSITE SHAPED ARTICLE

This is a division of application Ser. No. 917,194 filed Oct. 9, 1986 which is a division of Ser. No. 675,997 filed Nov. 29, 1984, now U.S. Pat. No. 4,686,124.

BACKGROUND OF THE INVENTION

1. Field of the Invention

This invention relates to a thermoplastic resin-silicone composite shaped article comprising a layer of a thermoplastic resin and a cured layer of an addition polymerization type silicone composition in the form of a laminate of these layers. The present invention is to provide new and useful medical devices made from the above composite shaped article, such as blood bag, medical tube and the like.

2. Description of the Prior Art

In general, silicone polymers are superior in thrombus resistance and histocompatibility and have been expected as a medical material. However, they are used only in a limited amount in medical field because of their high cost and low mechanical strength.

Of thermoplastic resins being used in medical applications, soft vinyl chloride resins, by the addition of a plasticizer, a high molecular elastomer or the like, have flexibility, excel in transparency, and are good in adhesion and processability by high frequency or other method. However, the soft vinyl chloride resins have a hygienic problem of dissolution of plasticizer and the like into an adjacent liquid and, moreover, are inferior in thrombus resistance, histocompatibility, etc.

Olefin resins, particularly, polyethylene, polypropylene and ethylene-propylene copolymers are inexpensive and are superior in toughness and rigidity. However, they are insufficient in flexibility and thrombus resistance.

Urethane resins excel in toughness and flexibility; however most of them are low in rigidity and all urethane resins except segmented ones are insufficient in thrombus resistance.

Styrene resins excel in transparency and rigidity and are widely used in medical utencils, food packaging, etc. However, they are insufficient in flexibility and poor in thrombus resistance.

Thus, silicone polymers and various thermoplastic resins now in use in medical applications each have strong points and weak points. Therefore, various attempts have been made of using two or more of these materials as one composite material.

Conventional silicone rubbers and resins are generally inactive and poor in adhesivity. Their adhesion to other resins is not sufficient even if they contain polar group-containing components present in condensation type RTV silicones or in so-called self-adhering silicones disclosed in Japanese Patent Application Kokai (Laid-Open) No. 24258/77, etc.

With respect to vinyl chloride resins, particularly, soft vinyl chloride resins, it has been generally thought that their strong adhesion to silicone polymers is difficult due to the effect of additives contained in the vinyl chloride resins such as a stabilizer, a plasticizer and the like. In order to overcome this drawback, there were proposed various methods in which the surface of a soft vinyl chloride resin is treated, for example, with a primer and then a silicone layer is formed thereon. However, these methods had drawbacks in that (a) the process are complex, (b) many primers use a solvent such as ethyl acetate, toluene or the like and the solvent may remain partly and (c) the adhesion between the vinyl chloride resin and the silicone layer causes separation with the lapse of time.

Japanese Patent Application Kokai (Laid-Open) No. 156083/79, etc. proposed a method wherein the surface of a vinyl chloride resin is subjected to low temperature plasma treatment and then thereon is formed a cured layer of a condensation type RTV silicone. Japanese Patent Application Kokai (Laid-Open) No. 32773/83 proposed the modification of a vinyl chloride resin material in which the surface of the vinyl chloride resin material is subjected to plasma treatment or the like to form a cured layer and then thereon is formed a silicone resin layer composed of a dimethylpolysiloxane or an alkyl group-modified dimethylpolysiloxane. From these methods, it is clear that a silicone resin can be allowed to adhere to the surface of a vinyl chloride resin. However, it is difficult to subject the inner surface of a small diameter tube or a long tube made of a vinyl chloride resin material to a complete low temperature plasma treatment to form a cured layer.

Olefin resins are crystalline resins of no polarity and are hardly soluble in solvents. Therefore, their adhesion to metals or plastics is very difficult. Their strong adhesion particularly to silicones have been thought to be almost impossible.

Hence, in order to obtain adhesion between an olefin resin and a silicone, there were made various attempts in which (1) the surfaces of the olefin resin and the silicone are each subjected to a physical treatment such as corona discharge or the like or to a chemical treatment by a bichromic acid-sulfuric acid mixture or the like to cause surface oxidation and form an oxide film containing polar groups such as carbonyl group and the like and then (2) these two treated surfaces are allowed to adhere to each other by the use of an adhesive of epoxy-polyamide, nitrile rubber, isocyanate, cyanoacrylate or other type. In any of these attempts, however, no practically usable adhesion could be achieved.

Methods for adhesion between various base materials and silicones via various primers are described in Japanese Patent Application Kokai (Laid-Open) No. 23667/82, Japanese Patent Application Kokai (Laid-Open) No. 162711/82, etc. However, no reporting has been made yet regarding strong adhesion between thermoplastic resins such as urethane resins and styrene resins and addition polymerization type silicones without requiring the above primer treatment which is complicated.

Thus, use of composite materials between thermoplastic resins and silicone polymers have been strongly desired; however no such materials which can be put into practical applications have been available.

With respect to soft vinyl chloride resins which contain a plasticizer, etc., dissolution of the plasticizer, etc. into an adjacent liquid has been a concerned matter. However, no effective method for overcoming the problem has been established yet. For example, in Japanese Patent Application Kokai (Laid-Open) No. 116469/81, it is reported that plasticizer dissolution can be reduced by subjecting the surface of a soft vinyl chloride resin to low temperature plasma treatment. However, the plasma treatment is extremely difficult for shaped articles of long tube configuration particularly with a small inner diameter. Also, it is said that the plasma treatment deteriorates the biocompatibility of soft vinyl chloride resins. Therefore, the plasma treatment for soft vinyl chloride resins has not been put into practical application.

SUMMARY OF THE INVENTION

The object of this invention is to produce from (a) thermoplastic resins (soft vinyl chloride resins, olefin resins, urethane resins and styrene resins) which are in wide use as medical devices or packaging materials for several excellent characteristics despite some weak points and (b) silicone rubbers which are expensive and insufficient in strength but superior in biocompatibility, etc., a composite shaped article between the materials (a) and (b) in which the strong points of the materials (a) and (b) are utilized and their weak points are made up for and are suitable for medical applications.

The present inventors made extensive study with a view to obtain an excellent composite shaped article between (a) thermoplastic resins (soft vinyl chloride resins, olefin resins, urethane resins and styrene resins) having various excellent characteristics and (b) silicones superior in biocompatibility, etc. As a result, it was found that surprisingly there are combinations of resins in which a thermoplastic resin of vinyl chloride, olefin, urethane or styrene type and a silicone can strongly adhere to each other. By further continuing the above study, a useful composite shaped article of the present invention has been completed.

According to the present invention, there is provided a thermoplastic resin-silicone composite shaped article comprising (a) a shaped article of a thermoplastic resin selected from the group consisting of soft vinyl chloride resins, olefin resins, urethane resins and styrene resins (the resin is hereinafter referred simply to as a thermoplastic resin) and (b) a cured layer or cured layers or an addition polymerization type silicone composition adhering to at least one surface of said shaped article. The present invention further provides a multilayer laminate comprising (a) at least two layers of the above mentioned shaped article of a thermoplastic resin and (b) at least one cured layer of an addition polymerization type silicone composition, wherein (1) said layers of the shaped article of a thermoplastic resin adhere to each other through said cured layer of an addition polymerization type silicone composition, (2) the outermost layers of said laminate are the layer (s) of said shaped article of a thermoplastic resin and/or the cured layer(s) of said addition polymerization type silicone composition, and (3), when the outermost layer(s) of said laminate is (are) the cured layer(s) of said addition polymerization type silicone composition, a layer (layers) of a material selected from the group consisting of thermoplastic resins other than said thermoplastic resin, silicone rubbers, silicone resins, glass, ceramics and metals may further adhere to the outermost layer(s). More specifically, the present invention provides a multilayer blood bag consisting of at least two layers of a thermoplastic resin layer and a cured layer of an addition polymerization type silicone composition wherein the cured layer of an addition polymerization type silicone composition comes into direct contact with blood; a catheter tube with a balloon, characterized in that the catheter tube and the balloon are made from a same or different thermoplastic resin or a silicone rubber and, at the balloon-fixing portion of the catheter, are laminated into one integral body with an addition polymerization type silicone composition; and a composite shaped article wherein a soft vinyl chloride resin an addition polymerization type silicone and an ethylene-vinyl alcohol copolymer, or, a soft vinyl chloride resin, an addition polymerization type silicone, an ethylene-vinyl alcohol copolymer and an addition polymerization type silicone are laminated in this order to greatly reduce the dissolution of a plasticizer contained in the soft vinyl chloride resin into a liquid which will come into contact with the composite shaped article.

DETAILED DESCRIPTION OF THE INVENTION

In the present invention, the soft vinyl chloride resins are compositions each comprising (1) a main component of a vinyl homopolymer or a copolymer composed essentially of vinyl chloride such as a vinyl chloride-ethylene copolymer, a vinyl chloride-vinyl acetate copolymer, a vinyl chloride-ethylene-vinyl acetate terpolymer, a vinyl chloride-(meth)acrylate copolymer, a vinyl chloride-urethane copolymer or the like, (2) a plasticizer which imparts flexibility to the main component and (3) other components.

As the plasticizer, there can be used, for example, aliphatic dibasic acid esters (e.g. dioctyl phthalate, dioctyl adipate, dibutyl sebacate), polyester type plasticizers, epoxidized soybean oil, epoxidized linseed oil, etc. Use of these plasticizers in 100 phr by weight or more relative to the resin tends to reduce the bonding strength of the soft vinyl chloride resin to an addition polymerization type silicone composition. When the amount of a plasticizer added is less than 100 phr by weight, a fairly wide range of vinyl chloride resins from hard type to soft type can be practically used. Therefore, a past general concept that adhesion between a soft vinyl chloride resin and a silicone is extremely difficult has been overthrown by the present invention. Of these plasticizers, phthalic acid esters such as dioctyl phthalate, epoxidized soybean oil and epoxidized linseed oil can retain the bonding strength of the soft vinyl chloride resin fairly well and therefore they are particularly preferred plasticizers. Besides, non-liquid high molecular substances capable of imparting flexibility to vinyl chloride resins, such as urethane polymers, ethylene-vinyl acetate copolymers and the like can also be used as plasticizers.

Further, as a stabilizer for imparting heat resistance and heat stability, there can be used in the soft vinyl chloride resin of the present invention (1) metal soaps composed of a metal such as Ca, Zn, Pb, Ba, Mg, Al or the like and a higher fatty acid such as stearic acid, (2) organometal and inorganic metal stabilizers of the above metals, (3) organotin type stabilizers, (4) organic silicon type stabilizers, and (5) ester type stabilizers such as butyl stearate and the like. Of these, there are preferred metal soaps such as Ca stearate, Zn stearate, Pb stearate, Ba stearate and the like as well as organometal and inorganic metal stabilizers of the above metals. Organotin type stabilizers are effective only when a plasticizer is used in a small amount, and they may reduce the bonding strength between a vinyl chloride resin and an addition polymerization type silicone composition when the plasticizer is contained in 50 phr or more. Ester type stabilizers (e.g. butyl stearate) and phosphoric acid type stabilizers inhibit the curing of a silicone composition when they are used in combination, and therefore, these two types of stabilizers cannot be used in combination.

In the vinyl chloride resin, there can also be used additives such as an ultraviolet inhibitor, a pigment, an antistatic agent, an X-ray contrast medium and the like. As a lubricant for imparting lubricity, there can be used higher fatty acids, higher alcohols, low molecular polyethylenes, amides, esters and the like. Higher fatty acids as lubricant, such as stearic acid and the like tend to plate out on the surface of the vinyl chloride resin, and therefore, their amounts must be restricted. Lubricants such as stearic acid and the like are used preferably in an amount of 0.5 phr or less, particularly when they are used in combination with barium sulfate employed in medical field as an X-ray contrast medium, bismuth subcarbonate, etc.

As described above, widely known components are used in the soft vinyl chloride resin of the present invention.

In the present invention, the olefin resins are low density polyethylenes, medium density polyethylenes, high density polyethylenes linear low density polyethylenes, polypropylenes, ethylene-propylene block copolymers, ethylene-propylene random copolymers, ethylene-propylene-diene terpolymers, ethylene-vinyl acetate copolymers, ethylene-vinyl alcohol copolymers, ionomer resins, polybutadienes, butadiene copolymers, etc. They are used as a single polymer or a mixture of two or more. Those polymers having a relatively large amount of unsaturated double bonds within the molecules are preferred. Polyethylenes originally have a molecular structure of $CH_2$ straight chain as shown in the formula (1). There are many cases that they contain in their molecules unsaturated double bonds as shown in the formulas (2), (3) and (4), depending upon the polymerization conditions, etc. As is well known, the presence of vinyl group at the molecular ends is confirmed even in high density polyethylenes by infrared spectrophotometry. It is preferable that the olefin resins of the present invention contain as many unsaturated double bonds as possible in their molecules.

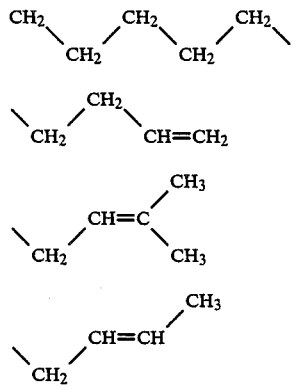

In the present invention, the urethane resins refer to resins having urethane bonds such as polyurethane resins, thermoplastic polyurethane elastomers and the like as well as to urethane copolymers such as urethanesilicone copolymers and the like. Further, there are included polyurethanes having crosslinked structures such as room temperature setting type polyurethanes and the like.

In the present invention, the styrene resins refer to polystyrenes, styrene copolymers (e.g. styrene-butadiene copolymers, styrene-acrylonitrile copolymers, styrene-methyl methacrylate copolymers, acrylonitrile butadiene-styrene terpolymers), polymers of styrene derivatives such as methylstyrene, dichlorostyrene and the like, and blends comprising essentially a polystyrene such as high impact polystyrene. It is generally thought that styrene polymerization reaction proceeds similarly to the chain reaction of a monomer having a vinyl group. Therefore, it is thought that styrene resins contain unsaturated double bonds as vinyl chloride resins do. The presence of as many unsaturated double bonds as possible is preferred.

In the present invention, the addition polymerization type silicone compositions are compositions each consisting of (a) a polysiloxane having vinyl groups represented by the formula (5),

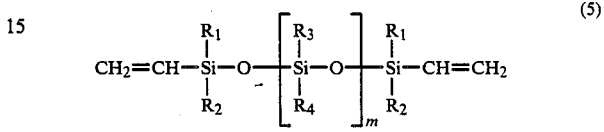

wherein $R_1$, $R_2$, $R_3$ and $R_4$ may be same or different and are each a monovalent hydrocarbon group having 6 or less carbon atoms and m is a positive integer, (b) an organohydrogenpolysiloxane represented by the formula (6),

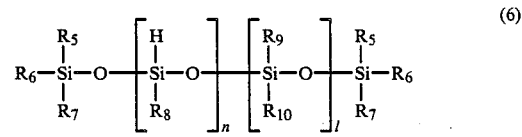

wherein $R_5$, $R_7$, $R_8$, $R_9$ and $R_{10}$ may be same or different and are each a monovalent hydrocarbon group having 6 or less carbon atoms, two $R_6$'s each are a hydrogen atom or a same or different monovalent hydrocarbon group having 3 or less carbon atoms, n is an integer of 2 to 100 and l is an integer of 0 to 100, and (c) an inorganic substance as a reinforcing component such as silica or the like. The compositions can be converted into a solid elastomer when subjected to addition polymerization in the presence of a platinum type catalyst.

The present inventors found that an addition polymerization type silicone composition can have a very high adhesion strength toward a vinyl chloride resin if the silicone composition contains an organohydrogenpolysiloxane represented by the formula (6) having at least two hydrogen atoms directly bonded to silicon atoms in each molecule, in an amount enough to provide one to six such hydrogen atoms per one vinyl group in the formula (5).

A similarly high bonding strength can also be obtained by a silicone composition containing at least one compound selected from components contained in so-called self-adhering silicone rubbers, namely, epoxy compounds, carboxylic acid anhydrides, silanes or siloxanes having an acryloxyalkyl group represented by the general formula (7),

wherein R is $CH_3$ or a hydrogen atom and n is an integer of 1 to 3, and unsaturated hydrocarbon group-containing oxysilane compounds, if the above silicone composition contains an organohydrogenpolysiloxane represented by the formula (6) having at least two hydrogen atoms directly bonded to silicon atoms in each molecule, in an amount enough to provide one to six such hydrogen atoms per one vinyl group in the formula (5). The presence of these adhesion improvers further enhances the bonding strength of an addition polymerization type silicone composition.

The strength of the cured layer of an addition polymerization type silicone composition of the present invention can be enhanced by incorporating into the composition a resinous copolymer containing vinyl groups which is dissolved in components of the formulas (5) and (6). As one example of such a copolymer, there is an organopolysiloxane obtained from copolymerization of the following formulas (8), (9) and (10), $$(CH_2=CH)(R_{11})(R_{12})SiO_{0.5} \quad (8)$$

$$SiO_2 \quad (9)$$

$$(R_{13})_3SiO_{0.5} \quad (10)$$

In the above formulas, $R_{11}$, $R_{12}$ and $R_{13}$ may be same or different and are each a monovalent hydrocarbon group having 6 or less carbon atoms.

As described in Japanese Patent Publication Nos. 45098/80 and 33256/78, Japanese Patent Application Kokai (Laid-Open) Nos. 126455/77 and 101884/79, U.S. Pat. No. 3,527,655 and other literature references, it is a known fact that compositions between an addition polymerization type silicone and other various components adhere strongly to metals, ceramics, glass and such resins as those having polar groups (e.g. epoxy resins, polyesters, polymethyl methacrylate, polycarbonates, polyamides). However, there has hitherto been no reporting that these addition polymerization type silicone compositions adhere strongly to resins having no polar group such as soft vinyl chloride resins, olefin resins, styrene resins, urethane resins and the like without using a primer or the like. Rather, adhesion between a silicone and these thermoplastic resins has been thought to be extremely difficult.

Thus, it is absolutely necessary in the present invention that, for strong adhesion to thermoplastic resins, an addition polymerization type silicone composition contain an organohydrogenpolysiloxane having at least two hydrogen atoms bonded directly to silicon atoms in each molecule, in an amount enough to provide excessive (1 to 6) such hydrogen atoms per one vinyl group of the silicone composition. However, when the very surface of a thermoplastic resin to which an addition polymerization type silicone composition is allowed to adhere is subjected beforehand to low temperature plasma treatment, corona discharge, ultraviolet irradiation or the like, because the surface is given polarity by such treatment, the addition polymerization type silicone composition can contain the above-mentioned organohydrogenpolysiloxane in a lesser amount, namely, an amount to provide about 0.8 to 6 hydrogen atoms directly bonding with silicon atoms per one vinyl group of the silicone composition and still a sufficient adhesion strength is secured. Also when a thermoplastic resin to which an addition polymerization type silicone composition is allowed to adhere contains 0.1 to 10 parts by weight, relative to 100 parts by weight of the resin, of a thermoplasticity-imparting resin having a number mean polymerization degree of 3 to 200 and having at least one carbon-carbon double bond per three polymerization units, the addition polymerization type silicone composition can contain the above-mentioned organohydrogenpolysiloxane in a smaller amount, namely, an amount to provide about 0.8 to 6 hydrogen atoms directly bonded to silicon atoms per one vinyl group of the silicone composition and still a sufficient bonding strength is secured.

As the above-mentioned thermoplasticity-imparting resin having C—C double bonds in the molecule, there are mentioned diallyl phthalate prepolymers, polybutadienes, etc. Any thermoplasticity-imparting resin can be used if it has a number mean polymerization degree of 3 to 200 and at least one C—C double bond per three polymerization units. When the number mean polymerization degree is less than 3, the thermoplasticity-imparting resin tends to cause plate-out from the surface of a thermoplastic resin in which it is contained, resulting in reduced adhesivity. When the number mean polymerization degree exceeds 200, the compatibility between the thermoplasticity-imparting resin and a thermoplastic resin is reduced.

In the present invention, when a thermoplastic resin contains an organohydrogenpolysiloxane having at least 30 mole % of an organohydrogensiloxane unit in an amount of 0.01 to 10 parts by weight relative to 100 parts by weight of the resin, because the resin contains the organohydrogensiloxane unit thought to be closely connected with adhesivity between a thermoplastic resin and a silicone, in a sufficient amount, the thermoplastic resin can be allowed to adhere to an addition polymerization type silicone composition whose component formulation can vary fairly widely, that is, an addition polymerization type silicone composition containing an organohydrogenpolysiloxane having at least two hydrogen atoms directly bonded to silicon atoms in each molecule, in an amount to provide 0.6 to 6 such hydrogen atoms per one vinyl group of the silicone composition.

As described above, an adhesivity of a thermoplastic resin toward an addition polymerization type silicone composition can be improved by a surface treatment such as plasma treatment, addition of an organohydrogenpolysiloxane, or addition of a thermoplasticity-imparting resin having carbon-carbon double bonds. However, even if a thermoplastic resin is improved in adhesivity by one of the above methods, if the thermoplastic resin contains such substances as impair the curing of an addition polymerization type silicone composition to which the thermoplastic resin is allowed to adhere, namely, an organotin type stabilizer and the like, in a relatively large amount, inhibitory actions of these substances reduce adhesivity between the thermoplastic resin and the silicone composition and obtainment of sufficient adhesion is difficult.

Specific useful applications of the thermoplastic resin-silicone composite shaped article of the present invention will be described.

The composite shaped article of the present invention can be used as a catheter wherein the surface of a shaped article of a thermoplastic resin according to the present invention is coated with an addition polymerization type silicone composition of the present invention, as a membrane for oxygenerators or for gas enrichment wherein a porous or fibrous film composed of a thermoplastic resin of the present invention is coated with an addition polymerization type silicone composition of the present invention, and as a multilayer blood bag wherein one layer coming into direct contact with blood is an addition polymerization type silicone composition of the present invention and the other layer is a thermoplastic resin of the present invention. This blood bag improves the drawbacks of conventional blood bags, is tough and transparent, and is superior in long term storage of blood and property of platelet-adhering. Also, a composite bag consisting of a polyester, nylon, a thermoplastic resin of the present invention and an addition polymerization type silicone composition of the present invention can be provided by the present invention for use as a heat-resistant bag such as a retort pouch.

Further, there can be provided a catheter tube with a balloon wherein the catheter tube and the balloon are each made of a same or different thermoplastic resin or silicone rubber and, at the balloon-fixing portion of the catheter tube, the catheter tube and the balloon are bonded strongly with an addition polymerization type silicone composition of the present invention. This catheter tube with a balloon enables wide and flexible selection for material combination of tube main body and balloon. For example, there can be provided a Sengstaken-Blakemore tube wherein a balloon of silicone rubber is fixed to a tube of soft vinyl chloride resin, as well as a dilation catheter wherein a balloon of polyethylene is fixed to a tube of soft vinyl chloride resin. These material combinations have not hitherto been employed and are novel in the present invention. Thus, the present invention can provide various catheter tubes with a balloon for medical use. By applying this technique, it becomes possible as necessary that a cured layer of an addition polymerization type silicone composition of the present invention is provided only at the balloon-fixing portion of a tube made of an urethane resin, a soft vinyl chloride resin or the like and, on the cured layer, there is fixed a balloon made of a silicone rubber, with a condensation type RTV silicone.

Furthermore, the present invention can provide a thermoplastic resin-silicone composite shaped article wherein plasticizer dissolution from the soft vinyl chloride resin layer into liquid adjacent to the composite article is greatly reduced. This composite shaped article is a laminate of a soft vinyl chloride resin, an addition polymerization type silicone and an ethylene-vinyl alcohol copolymer or of a soft vinyl chloride resin, an addition polymerization type silicone, an ethylene-vinyl alcohol copolymer and an addition polymerization type silicone in this order and is characterized in that the permeation of plasticizer through the laminate is prevented or suppressed by the ethylene-vinyl alcohol copolymer layer.

It is a known fact that ethylene-vinyl alcohol copolymers have an excellent barrier property for oxygen gas. It is also known, however, that the copolymers are relatively high in moisture uptake and, once they have absorbed moisture, the barrier property is greatly reduced. The present inventors found that ethylene-vinyl alcohol copolymers, regardless of whether they are in a dry state or in a moisture-wet state, are very resistant to the permeation of plasticizers such as dioctyl phthalate and the like. Based on this finding and also on a knowledge that an ethylene-vinyl alcohol copolymer can adhere strongly to an addition polymerization type silicone, the present invention has been completed.

The above composite shaped article comprises (a) a base layer made of a tough and flexible soft vinyl chloride resin, (b) an ethylene-vinyl alcohol copolymer layer capable of greatly suppressing the permeation of a plasticizer from the soft vinyl chloride resin and (c) an outermost layer made of a silicone rubber or an ethylene-vinyl alcohol copolymer. Hence, the composite shaped article has excellent biocompatibility and can be very suitably used in medical applications.

The thermoplastic resin-silicone composite shaped article of the present invention has wide applications also in various industrial fields. For example, soft vinyl chloride resins or polyolefins, for both of which it has been said that there is no effective adhesive, can have strong adhesion among themselves by the use of an addition polymerization type silicone composition. This enables connection between industrial pipes made of the above resins. The resulting connected pipes are included in the composite shaped article of the present invention. Also, an addition polymerization type silicone composition can be utilized as a surface-protecting film for thermoplastic substrate materials used in electronics field. These surface-protected substrate materials are also included in the composite shaped article of the present invention.

As described above, the composite shaped article of the present invention can be widely used in medical field, various industrial fields, etc.

The detailed mechanism of adhesion between a thermoplastic resin and an addition polymerization type silicone composition in the thermoplastic resin-silicone composite shaped article of the present invention is not clear. As one possible mechanism, it can be surmised that the organohydrogensiloxane group of the addition polymerization type silicone composition reacts with the functional group of the thermoplastic resin. This can be surmised also from our finding that a higher content of the organohydrogensiloxane group gives a higher bonding strength. As the functional group of the thermoplastic resin of the present invention, there are considered C—C double bonds such as vinyl group and, in this case, there probably occurs an addition reaction between the organohydrogensiloxane group and the C—C double bond. As previously desired, it is thought that a fairly large amount of unsaturated double bonds remains particularly in vinyl chloride resins, olefin resins, styrene resins, etc. With respect to urethane resins, the presence of C—C double bonds will not be probable. Adhesion of an urethane resin to an addition polymerization type silicone composition will be due to a reaction between the urethane bond and the organohydrogensiloxane group or to an affinity between the polar group of the urethane resin and the organohydrogensiloxane group.

Thus, the mechanism of adhesion between an addition polymerization type silicone composition of the present invention and a thermoplastic resin of the present invention has not been thoroughly clarified; however the organohydrogensiloxane group of the addition polymerization type silicone composition is surmised to be the most important contribution.

Next, a process for producing the thermoplastic resin-silicone composite shaped article of the present invention will be described. There is no particular restriction for this process. A desirable example of the process is as follows: That is, on the surface of a thermoplastic resin shaped article of the present invention, there is laminated an addition polymerization type silicone composition of the present invention or a solution of the composition dissolved in an organic solvent, by a method such as coating, dipping, spraying or the like. Then, this integral body is subjected to heat treatment at 40° to 130° C., preferably 80° to 120° C. for 5 min to 10 hr, preferably 10 min to 3 hr, whereby a cured layer is formed on the thermoplastic resin shaped article. Certain kinds of addition polymerization type silicone compositions using a chloroplatinic acid catalyst can cure in a time period as short as 30 sec at 100° C. to form a desired film; however in such a short time, no sufficient adhesion strength can be obtained with thermoplastic resins. Certain other kinds of addition polymerization type silicone compositions containing a platinum type catalyst can cure in 5 min to 3 days at 30° C.; however no sufficient adhesion strength can be obtained as well. Reasons for these poor bonding strengths will be that, in these kinds of addition polymerization type silicone compositions, the reaction between their hydrogen atoms directly bonded to silicone atoms and C—C double bonds of the thermoplastic resins is greatly dependent upon the reaction temperature and the reaction time.

The cured layer of the addition polymerization type silicone composition thus formed adheres very strongly to the surface of the thermoplastic resin shaped article of the present invention. This adhesion does not deteriorate with the lapse of time and also even after a severe treatment such as autoclave or the like.

EXAMPLE 1

Adhesivities between various thermoplastic resins and various silicones were investigated in accordance with JIS K 6301. Each thermoplastic resin was kneaded at 170° to 200° C. for 3 to 5 min by the use of an 8 in. roll and then press-molded at 170° to 200° C. for 2 to 7 min to obtain sheets each of 20 mm×50 mm×1 mm. Between two of these sheets, there was placed an addition polymerization type silicone in a thickness of 1 mm. They were heated at 80° to 110° C. for 60 to 90 min to obtain a test specimen for adhesion test. All test specimens thus obtained were subjected to 180° peeling test by the use of universal tensile testing instrument. The results are shown in Table 1.

TABLE 1

| Thermoplastic resin *1 | | Example | | Comparative Example | |
|---|---|---|---|---|---|
| | | Silicone *2 | | | |
| | | Addition polymerization type silicone | | Condensation type RTV silicone | |
| | | A | B | C | D |
| Soft vinyl chloride resin | A | 2.8 | 4.0 | 0.1 | 0.1 |
| | B (Plasma-treated A) | 4.0 | — | 0.3 | 0.9 |
| Olefin resin | A | 2.7 | 3.0 | 0.1 | 0.1 |
| | B | 2.1 | 2.4 | 0.1 | 0.1 |
| Urethane resin | A | 2.9 | 3.9 | 0.1 | 0.2 |
| | B | 2.8 | 4.0 | 0.1 | 0.1 |
| Styrene resin | A | 3.1 | 3.2 | 0.2 | 0.2 |
| | B | 2.9 | 3.1 | 0.1 | 0.1 |

Unit: kg/cm

Note:  indicates cohesive failure of silicone layers.
*1 Thermoplastic resins:
Soft vinyl chloride resin A
This resin was prepared by adding, to 100 parts by weight of a vinyl chloride resin (SX-DH, manufactured by SUMITOMO CHEMICAL CO., LTD.), 50 parts by weight of dioctyl phthalate, 0.025 part by weight (as metal) of Zn stearate, 0.025 part by weight (as metal) of Ca stearate and 10 parts by weight of epoxidized soybean oil.
Soft vinyl chloride resin B
This resin was prepared by subjecting sheets of the soft vinyl chloride resin A to low temperature plasma treatment under the following conditions. The sheets of the soft vinyl chloride resin A were placed in a chamber. The chamber inside pressure was made vacuum to 0.05 Torr

TABLE 1-continued and argon gas was introduced into the chamber at a rate of 300 ml/min, whereby the chamber inside pressure was made at about 0.15 Torr. Then, discharging was allowed to occur for 5 min inside the chamber by the use of high frequency internal electrodes with a voltage of 700 W applied between the electrodes, whereby the surfaces of the soft vinyl chloride resin A sheets were subjected to plasma treatment.
Olefin resin A
A low density polyethylene (SUMIKATHENE F 208, manufactured by SUMITOMO CHEMICAL CO., LTD.)
Olfein resin B
A polypropylene (SUMITOMO NOBLEN FL-6315, manufactured by SUMITOMO CHEMICAL CO., LTD.)
Urethane resin A
A thermoplastic polyurethane (TAKELAC T-895, manufactured by Takeda Chemical Industries, Ltd.)
Urethane resin B
A segmented polyurethane (Pellethene, manufactured by Upjohn Co.)
Styrene resin A
A polystyrene (HH 30, manufactured by Idemitsu Petrochemical Co., Ltd.)
Styrene resin B
A polystyrene (HT 50, manufactured by Idemitsu Petrochemical Co., Ltd.)
*2 Addition polymerization type silicones:
Silicone A
This silicone was prepared by adding, to 100 parts by weight of a dimethylpolysiloxane having dimethylvinylsilyl groups at both ends of the molecular chain and having a viscosity of 18,000 cs at 25° C., 5 parts by weight of a polysiloxane consisting of 10 mole % of a trimethylsiloxane unit, 40 mole % of a dimethylsiloxane unit and 50 mole % of a methylhydrogensiloxane unit, 20 parts by weight of silica and 0.2 part by weight of an isopropyl alcohol solution of chloroplatinic acid (1% of platinum in the solution).
Silicone B
This silicone was prepared by adding, to 100 parts by weight of a dimethylpolysiloxane having dimethylvinylsilyl groups at both ends of the molecular chain and having a viscosity of 1,300 cs at 25° C., 15 parts by weight of a conventionally known copolymer consisting of a $(CH_3)_3SiO_{0.5}$ unit, a $(CH_2=CH)(CH_3)_2SiO_{0.5}$ unit and a $SiO_2$ unit wherein the ratio of (1) the sum of the number of $(CH_3)_3SiO_{0.5}$ units and the number of $(CH_2=CH)(CH_3)_2SiO_{0.5}$ units and (2) the number of $SiO_2$ units is 0.8:1 and the content of vinyl group is 0.9% by weight, 25 parts by weight of trimethylsilyl-treated silica in the form of aerosol, 5 parts by weight of a methylhydrogenpolysiloxane containing about 50 mole % of a methylhydrogensiloxane unit and having a viscosity of 50 cs at 25° C., 0.2 part by weight of an isopropyl alcohol solution of chloroplatinic acid (1% of platinum in the solution), 2 parts by weight of an epoxy compound having the following structural formula,

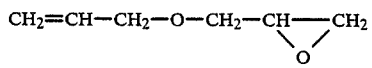

and 0.5 part by weight of phthalic anhydride.
Silicone C
A condensation type silicone (KE-42-RTV, manufactured by Shin-Etsu Chemical Co., Ltd.)
Silicone D
A condensation type silicone (KE-45-RTV, manufactured by Shin-Etsu Chemical Co., Ltd.)

EXAMPLE 2

Adhesivities between various thermoplastic resins containing organohydrogenpolysiloxanes and commercially available addition polymerization type liquid silicones were investigated in accordance with JIS K 6301. Each thermoplastic resin was kneaded at 170° to 200° C. for 3 to 5 min by the use of an 8 in. roll and then press-molded at 160° to 200° C. for 3 min to obtain sheets. Between two of these sheets, there was placed an addition polymerization type silicone in a thickness of 1 mm. They were heated at 80° to 110° C. for 60 to 90 min to obtain a test specimen for adhesion test. All test specimens thus obtained were subjected to 180° peeling test by the use of a universal tensile testing instrument. The results are shown in Table 2.

TABLE 2

Unit: kg/cm

| Thermoplastic resin * | | | Silicone Commercially available addition polymerization type liquid silicone | |
|---|---|---|---|---|
| | | | KE-1910 manufactured by Shin-Etsu Chemical Co., Ltd. | SE-6720 manufactured by TORAY SILICONE CO., LTD. |
| Soft vinyl chloride resin | 1 | Comparative Example | 0.1 | 0.3 |
| | 2 | Example | 3.2 | 3.5 |
| Olefin resin | 1 | Comparative Example | 0.5 | 0.6 |
| | 2 | Example | 0.2 | 0.1 |
| | 3 | Example | 4.1 | 4.3 |
| | 4 | | 3.9 | 4.2 |
| Soft vinyl chloride resin | 3 | Comparative Example | 0.1 | 0.2 |
| | | | 0.1 | 0.2 |
| | 4 | Example | 2.1 | 2.9 |

Note: ○ indicates cohesive failure of silicone layers.
* Thermoplastic resin:
Soft vinyl chloride resin 1
This resin was prepared by adding, to 100 parts by weight of a vinyl chloride resin (700 D, manufactured by TOYO SODA MANUFACTURING CO., LTD.), 0.04 part by weight (as metal) of Zn stearate, 0.02 part by weight (as metal) of Ca stearate, 50 parts by weight of dioctyl phthalate and 5 parts by weight of epoxidized soybean oil.
Soft vinyl chloride resin 2
This resin was prepared by adding, to 100 parts by weight of the soft vinyl chloride resin 1, 1.5 parts by weight of a n-hexane solution containing 70% by weight of an organohydrogenpolysiloxane represented by the formula (11),

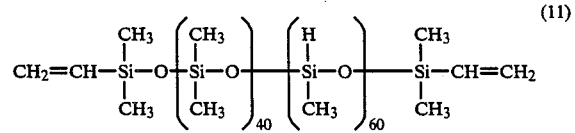
(11)

Olfein resin 1
A low density polyethylene (SUMIKATHENE F 101, manufactured by SUMITOMO CHEMICAL CO., LTD.)
Olfein resin 2
A polypropylene (SUMITOMO NOBLEN S-131, manufactured by SUMITOMO CHEMICAL CO., LTD.)
Olfein resin 3
This resin was prepared by adding, to 100 parts by weight of the olefin resin 1, 1.5 parts by weight of a n-hexane solution containing 70% by weight of the organohydrogenpolysiloxane represented by the formula (11).
Olefin resin 4
This resin was prepared by adding, to 100 parts by weight of the olefin resin 2, 1.5 parts by weight of a n-hexane solution containing 70% by weight of the organohydrogenpolysiloxane represented by the formula (11).
Soft vinyl chloride resin 3
This resin was prepared by adding, to 100 parts by weight of a vinyl chloride resin (700 D, manufactured by TOYO SODA MANUFACTURING CO., LTD.), 0.03 part by weight (as metal) of Zn stearate, 0.03 part by weight (as metal) of Ca stearate, 40 parts by weight of dioctyl phthalate and 10 parts by weight of epoxidized soybean oil.
Soft vinyl chloride resin 4
This resin was prepared by adding, to 100 parts by weight of the soft vinyl chloride resin 3, 0.5 part by weight of a diallyl phthalate prepolymer (DAISO DAP L, manufactured by OSAKA SODA CO., LTD.)

EXAMPLE 3

The following experiment was conducted to obtain a useful blood bag according to the present invention.

Bag 1

A composition consisting of 100 parts by weight of a vinyl chloride resin, 1.2 parts by weight of a Ca-Zn type composite stabilizer, 42 parts by weight of dioctyl phthalate and 8 parts by weight of epoxidized soybean oil was subjected to calendering to obtain a sheet of 0.3 mm thickness. One surface of this sheet was coated with a n-hexane solution containing a mixture of 100 parts by weight of a dimethylpolysiloxane having vinyl groups at both ends of the molecule and having a viscosity of 18,000 cp, 8 parts by weight of a polysiloxane whose methylhydrogenpolysiloxane component consists of 10 mole % of a trimethylsiloxane unit, 40 mole % of a dimethylsiloxane unit and 50 mole % of a methylhydrogensiloxane unit, 20 parts by weight of silica and 0.3 part by weight of an isopropyl alcohol solution containing chloroplatinic acid (1% platinum in solution), by the doctor blade method so that the thickness after curing became about 100μ. n-Hexane was removed and then the coated surface of the above sheet was covered by a teflon-coated glass-cloth paper. They were placed in a constant temperature bath at 110° C. for 2 hr for curing. Thereafter, on the silicone rubber side of the sheet was coated an undiluted addition polymerization type silicone rubber composition in a thickness of about 100μ so that the coated portion formed the fringe of a bag. Two of such sheets were put together so that respective coated sides faced each other. Between these two sheets was inserted an extruded tube (6 mm OD×4 mm ID) made of the abovementioned soft vinyl chloride resin, as a port. They were heat-cured at 110° C. for 2 hr in molding dies, whereby a Bag 1 was obtained.

Bag 2

A vinyl chloride resin sheet was prepared in the same manner as in the case of Bag 1. On the surface of this sheet which would later form the inner side of a bag, there was coated an addition polymerization type silicone composition in a thickness of about 50μ, and then the sheet was heated for curing. Thereafter, two of such sheets were put together so that respective coated sides faced each other and they were subjected to high frequency welding at the fringe portion of a bag shape by the use of an ordinary high frequency welding machine.

Bag 3

A resin composition consisting of 100 parts by weight of a polypropylene (SUMITOMO NOBLEN S-131, manufactured by SUMITOMO CHEMICAL CO., LTD.) and 20 parts by weight of a polyethylene (SUMIKATHENE F-208, manufactured by SUMITOMO CHEMICAL CO., LTD.) was extruded into a film of 100μ thickness. On one surface of this film, there was coated the addition polymerization type silicone composition used in the case of Bag 1, in a thickness of 100μ. After deaeration in vacuum, the coated surface of the film was covered by a teflon-coated glass-cloth paper. They were pressed at 115° C. for 1 hr, whereby a silicone rubber-polyolefin composite film was obtained. As in the case of Bag 1, the silicone rubber side of the film was coated with an addition polymerization type silicone composition so that the coated portion formed the fringe of a bag. Two of such sheets were put together so that respective coated sides faced each other. Between these two sheets, there was inserted as a port a vinyl chloride resin tube. They were heated at 110° C. for 1.5 hr, whereby a bag was obtained.

Bag 4

Two of the soft vinyl chloride resin sheets used in the case of Bag 1 were subjected to high frequency welding, whereby a bag for Comparative Example was obtained.

The bags thus obtained were subjected to sterilization treatment in an autoclave at 120° C. for 30 min. Into each of these bags, there was poured 50 ml of a dog's whole blood to which ACD had been added, and each bag was stored at 4° C. After 1, 4, 8, 24 and 48 hr, the number of platelets suspended in the blood was measured for each bag, from which a percentage of platelets decreased was calculated. Retention of red blood cells was investigated by counting the number of red blood cells in the blood after 24 hr storage.

TABLE 3

| | | Number of Platelets Suspended ($\times 10^4/mm^3$) | | | | | |
|---|---|---|---|---|---|---|---|
| | | Time of storage at 4° C. hr | | | | | |
| | | 0 | 1 | 4 | 8 | 24 | 48 |
| Example | Bag 1 | 15.9 | 15.7 | 15.9 | 16.5 | 14.6 | 12.8 |
| | Bag 2 | 15.8 | 15.8 | 15.6 | 15.3 | 14.2 | 11.8 |
| | Bag 3 | 15.2 | 16.3 | 15.1 | 14.8 | 15.0 | 13.4 |
| Comparative Example | Bag 4 | 16.3 | 14.4 | 13.7 | 11.9 | 12.7 | 10.3 |

| | Percentage of platelets survival |
|---|---|
| Comparative Example (Bag 4) | After 24 hr 77.9% |
| | After 48 hr 63.2% |
| Example (Bags 1 & 2) | After 24 hr 90.9% |
| | After 48 hr 77.6% |
| Example (Bag 3) | After 24 hr 98.7% |
| | After 48 hr 88.1% |

TABLE 4

| | | Retention of Red blood Cells ($\times 10^4/mm^3$) | | |
|---|---|---|---|---|
| | | 0 hr | After 24 days | Percentage of change (%) |
| Example | Bag 1 | 790 | 758 | −4.0 |
| | Bag 2 | 818 | 790 | −3.4 |
| | Bag 3 | 818 | 776 | −5.3 |
| Comparative Example | Bag 4 | 806 | 620 | −23.1 |

As is obvious from the Tables 3 and 4, blood bags according to the present invention were superior in retentions of both platelets and red blood cells.

The above bags had the physical properties shown in Table 5.

TABLE 5

| | | Autoclave characteristic | Peeling strength of the sealed portion (kg/20 mm width) | Tensile strength of sheet (kg/10 mm width) |
|---|---|---|---|---|
| Example | Bag 1 | Good | 6.4 | 7.8 |
| | Bag 2 | Good | 11.5 | 7.2 |
| | Bag 3 | Good | 7.2 | 9.4 |
| Comparative Example | Bag 4 | Partially tacked | 12.3 | 6.7 |

EXAMPLE 4

In this Example, there was produced a drainage tube used for percutaneous transhepatic cholangio drainage (PTCD) which is an effective remedy for obstructive jaundice. In the soft vinyl chloride resin composition used in Example 1, the amount of diethylhexyl phthalate was changed to 30 parts by weight and 100 parts by weight of a fine powder of barium sulfate was added as a contrast medium, whereby pellets were prepared. Those pellets were extruded into a tube of 3 mm in outside diameter and 1.5 mm in inside diameter having a fluid passage for balloon expansion of 0.3 mm in inside diameter. The front end of the tube was made smooth and the front end of the fluid passage for balloon expansion was sealed. At the balloon-fixing portion of the tube located in the vicinity of the front end of the tube, there was opened a side hole of 0.3 mm in diameter extending to the fluid passage for balloon expansion. Then, the balloon-fixing portion of the tube was covered with a balloon tube made of a silicone rubber and having an inside diameter of 3.2 mm, a thickness of 0.2 mm and a length of 15 mm. On a paste margin of about 4 mm in width on the balloon-fixing portion of the tube, there was coated an appropriate amount of the addition polymerization type silicone composition for adhesive use mentioned in Example 1. The balloon tube and the tube were allowed to adhere to each other by a heat-treatment at 100° C. for 2 hr. To the other end of the tube was allowed to adhere a branched connector connected with the fluid passage for balloon expansion and the tube bore, with cyclohexane. At the end of the connector branch connecting with the fluid passage for balloon expansion, there was equipped a check valve. At the portions of the tube in the vicinity of both ends of the balloon, there were opened two side holes of 0.8 mm in diameter extending to the tube bore.

In conventional drainage tubes, there have been used polyethylene or soft vinyl chloride resin tubes without balloon, or silicone rubber tubes with a silicone rubber balloon. The former tubes were rigid and could easily be inserted up to a bile duct percutaneously and transhepatically, however, have drawbacks in that there is no means for filling the tubes inside the bile duct and the tubes tend to be displaced out of the body due to the constantly occurring respiratory locomotion movement of liver and other reasons. The latter tubes can be tightly fixed inside the bile duct by expanding the balloon inside the bile duct and pressing the inner wall of the bile duct, however, they have a limitation that the tube main body and the balloon must be of the same material and, moreover, because the tube is a silicone rubber tube of relatively small outside diameter and accordingly is very low in rigidity, they buckle at the body surface at the time of insertion making the insertion difficult.

The drainage tube with a balloon according to the present invention has solved the drawbacks of the conventional drainage tubes. In the tube of the present invention, a flexible balloon is attached to a rigid tube; fixing inside the bile duct is conducted reliably; dislocation can be prevented; and tube insertion from the body surface is easy. Thus, the drainage tube with a balloon of the present invention is an ideal percutaneous transhepatic cholangio drainage tube.

EXAMPLE 5

The following experiment was conducted to produce a multilayer sheet of the soft vinyl chloride resin type from which plasticizer is leached out in only a very small amount.

To 100 parts by weight of a vinyl chloride resin (SX-DH, manufactured by SUMITOMO CHEMICAL CO., LTD.) were added 40 parts by weight of dioctyl phthalate, 0.03 part by weight (as metal) of a Ca type stabilizer, 0.03 part by weight (as metal) of a Zn type stabilizer and 10 parts by weight of epoxidized soybean oil. They were kneaded at 190° C. for 7 min by the use of a roll and then pressed at 200° C. for 3 min into a sheet of 1 mm in thickness. Separately, an ethylene-vinyl alcohol copolymer (Eval F, manufactured by KURARAY CO., LTD.) was extruded into a film of 50μ thickness by the use of an extruder.

The above soft vinyl chloride resin sheet was cut into 10 cm × 10 cm squares. On one side of each square sheet, there was coated an addition polymerization type silicone composition prepared by adding, to 100 parts of a dimethylpolysiloxane having dimethylvinylsilyl groups at both ends of the molecular chain and having a viscosity of 18,000 cs at 25° C., 5 parts by weight of a polysiloxane consisting of 10 mole % of a trimethylsiloxane unit, 40 mole % of a dimethylsiloxaee unit and 50 mole % of a methylhydrogensiloxane unit, 20 parts by weight of silica and 0.2 part by weight of an isopropyl alcohol solution of chloroplatinic acid (1% of platinum in solution), in a thickness of 50μ by the use of a spacer. Thereon was further placed the above prepared Eval film (cut into a 10 cm × 10 cm square), whereby a multilayer laminate A was prepared. On the Eval film of another multilayer laminate A, there was coated the above addition polymerization type silicone composition in a thickness of 50μ, whereby a multilayer laminate B was prepared. These two laminates A and B were placed in an oven and heated at 100° C. for 90 min, whereby soft vinyl chloride type multilayer laminates A and B were produced. These two laminates each had strong adhesion among layers and formed a complete integral body.

The multilayer laminates A and B as well as the above-mentioned soft vinyl chloride resin sheet as Comparative Example were each cut into a disc shape of 7 cm diameter. In accordance with JIS L 0821, each disc was set at the backside of a lid of a 500 ml metal container so that the soft vinyl chloride resin layer of the disc faced the backside of the lid. 100 ml of distilled water was placed in the metal container. After putting on the lid, the container was placed in a constant temperature bath of 40° C. and was given a vibration at 3 Hz for a given length of time, whereby the plasticizer, etc. contained in the soft vinyl choride resin layer were allowed to dissolve out into water. Thereafter, each extract was taken out and the amount of dioctyl phthalate in the extract was measured by gas chromatography. The results are shown in Table 6.

TABLE 6

| Tested laminate or sheet | | Amount of dioctyl phthalate dissolved (μg/ml) | | Trans-parency | Flexi-bility |
| --- | --- | --- | --- | --- | --- |
| | | 40° C. 1 hr | 40° C. 10 hr | | |
| Example | Multilayer laminate A | 11 | 38 | o | o |
| | Multilayer laminate B | 1> | 10 | o | o |
| Comparative Example | Soft vinyl chloride resin sheet | 95 | 254 | o | o |

In order to investigate thrombus resistances of the outermost surfaces of the multilayer laminates A and B and of the surface of the soft vinyl chloride resin sheet as Comparative Example, each laminate or sheet was cut into a 5 mm × 5 mm square. The square laminate or sheet was attached to the bottom of a glass-made flat Petri dish of 50 mm diameter by the use of a double-coated adhesive tape so that the surface to be evaluated of the laminate or sheet was directed upward. 5 ml of a dog's fresh blood was poured into the dish and the blood was incubated at 37° C. for 4 min. Then, the blood was gently removed from the dish with distilled water. The dish was treated with a 1% aqueous glutaraldehyde solution for 2 hr, washed with distilled water and air-dried. Thereafter, the surface of the laminate or sheet was observed by a scanning type electron microscope. The results are shown in Table 7.

TABLE 7

| Tested laminate or sheet | | Number of platelets attached per unit area (mm$^2$) (Observation by electron microscope) |
| --- | --- | --- |
| Example | Multilayer laminate A | $9.3 \times 10^4$ |
| | Multilayer laminate B | $1.2 \times 10^5$ |
| Comparative Example | Soft vinyl chloride resin sheet | $7.5 \times 10^5$ |

What is claimed is:

1. A multilayer laminate comprising a catheter and a balloon laminated into one integral body with an addition polymerization type silicone rubber composition (b) at a balloon-fixing portion of the catheter, wherein one of the catheter and the balloon is composed of a thermoplastic resin (a) selected from the group consisting of soft vinyl chloride resins (1), olefin resins (2), urethane resins (3), and styrene resins (4) and the other is composed of a material selected from the group consisting of soft vinyl chloride resins (1), olefin resins (2), urethane resins (3), styrene resins (4) and wherein the soft vinyl chloride resins (1) are selected from the group consisting of vinyl chloride homopolymer, a vinyl chloride-ethylene copolymer, a vinyl chloride-vinyl acetate copolymer, a vinyl chloride-ethylene-vinyl acetate terpolymer, a vinyl chloride-(meth)acrylate copolymer, and a vinyl chloride-urethane copolymer; the olefin resins (2) are selected from the group consisting of low density polyethylenes, medium density polyethylenes, high density polyethylenes, linear low density polyethylenes, polypropylenes, ethylene-propylene block copolymers, ethylene-propyllene random copolymers, ethylene-propylene-diene terpolymers, ethylene-vinyl acetate copolymers, ethylene-vinyl alcohol copolymers, ionomer resins, and polybutadienes; the urethane resins (3) are selected from the group consisting of crosslinking type polyurethane, and thermoplastic polyurethane elastomers; the styrene resins (4) are selected from the group consisting of polystyrene, styrene-butadiene copolymers, styrene-acrylonitrile copolymers, styrene-methyl methacrylate copolymers, acrylonitrile-butadiene-styrene terpolymers, poly-methylstyrene and polydichlorostyrene; and said silicone rubber compositions (b) consists of a mixture of (i) a polysiloxane having vinyl groups represented by the formula (5),

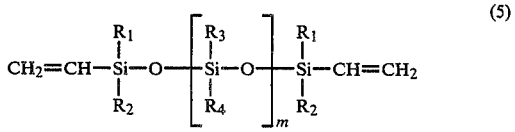

(5)

wherein $R_1$, $R_2$, $R_3$, and $R_4$ may be the same or different and are each a monovalent hydrocarbon group having 6 or fewer carbon atoms and m is a positive integer, (ii) an organohydrogenpolysiloxane represented by the formula (6),

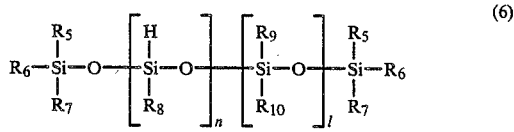

(6)

wherein $R_5$, $R_7$, $R_8$, $R_9$ and $R_{10}$ may be the same or different and are each a monovalent hydrocarbon group having 6 or fewer carbon atoms, two $R_6$'s each are a hydrogen atom or a same or different monovalent hydrocarbon group having 3 or fewer carbon atoms, n is an integer of 2 to 100 and l is an integer of 0 to 100, and (iii) an inorganic substance as reinforcing component, and the silicone rubber composition (b) is able to be converted into a solid elastomer when subjected to addition polymerization in the presence of a platinum catalyst and furthermore wherein the organohydrogenpolysiloxane (ii) has at least two hydrogen atoms directly bonded to silicon atoms in each molecule, and is present in the composition (b) in an amount sufficient to provide 0.6 to six such hydrogen atoms per one vinyl group of the silicone rubber composition.

2. A multilayer laminate according to claim 1, wherein the soft vinyl chloride resin (1) contains at least one stabilizer selected from the group consisting of higher fatty acid metal soaps, organometal stabilizers and inorganic metal stabilizers, and wherein the metal of said at least one stabilizer is calcium, zinc, lead, barium, magnesium or aluminum.

3. A multilayer laminate according to claim 1, wherein the addition polymerization type silicone rubber composition (b) further comprises, as components for improving its bonding strength, at least one compound selected from the group consisting of epoxy compounds, carboxylic acid anhydrides, siloxanes and silanes having an acryloylalkyl group represented by the formula:

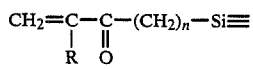

wherein R is $CH_3$ or a hydrogen atom and n is an integer of 1 to 3, and unsaturated hydrocarbon group-containing oxysilane compounds.

4. A multilayer laminate according to claim 1, wherein the surface of the thermoplastic resin (a) is subjected, prior to adhesion to said silicone rubber composition (b), to low temperature plasma treatment with an organohydrogenpolysiloxane including at least 30 mole % of an organohydrogensiloxane unit and the organohydrogenpolysiloxane (ii) in the composition (b) is present in the composition (b) in an amount sufficient to provide 0.8 to 6 such hydrogen atoms per one vinyl group of the silicone rubber composition.

5. A multilayer laminate according to claim 1, wherein the thermoplastic resin (a) includes 0.1 to 10 parts by weight, per 100 parts by weight of the resin, of a thermoplasticity-imparting resin having a mean polymerization degree of 3 to 200 and at least one carbon-carbon double bond per three polymerization units in the molecule, and the organohydrogenpolysiloxane (ii) in the composition (b) is present in the composition (b) in an amount sufficient to provide 0.8 to 6 such hydrogen atoms per one vinyl group of the silicone rubber composition.

6. A multilayer laminate according to claim 1, wherein the thermoplastic resin (a) includes 0.01 to 10 parts by weight, per 100 parts by weight of the resin (a), of an oragnohydrogenpolysiloxane having at least 30 mole % of an organohydrogensiloxane unit.

7. A multilayer laminate according to claim 1, wherein the organohydrogenpolysiloxane (ii) in the composition (b) contains at least one vinyl group.

* * * * *

UNITED STATES PATENT AND TRADEMARK OFFICE
CERTIFICATE OF CORRECTION

PATENT NO. : 4,834,721

DATED : May 30, 1989

INVENTOR(S) : ONOHARA et al.

It is certified that error appears in the above-identified patent and that said Letters Patent is hereby corrected as shown below:

Column 18, line 59, before the word "wherein", insert --silicone rubber--.

Signed and Sealed this

Fifth Day of January, 1993

Attest:

DOUGLAS B. COMER

Attesting Officer

Acting Commissioner of Patents and Trademarks